United States Patent
Lippolis et al.

(10) Patent No.: US 8,785,421 B1
(45) Date of Patent: Jul. 22, 2014

(54) USE OF VITAMIN D IN DAIRY MASTITIS TREATMENT

(75) Inventors: John D. Lippolis, Ames, IA (US); Timothy A. Reinhardt, Ames, IA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 349 days.

(21) Appl. No.: 13/434,985

(22) Filed: Mar. 30, 2012

Related U.S. Application Data

(60) Provisional application No. 61/473,208, filed on Apr. 8, 2011.

(51) Int. Cl.
*A61K 33/06* (2006.01)

(52) U.S. Cl.
USPC .......................................... 514/165; 514/167

(58) Field of Classification Search
USPC ................................................. 514/165, 167
See application file for complete search history.

(56) References Cited

U.S. PATENT DOCUMENTS

| | | | |
|---|---|---|---|
| 3,646,203 A | 2/1972 | De Luca | 514/167 |
| 4,338,312 A | 7/1982 | DeLuca et al. | |
| 4,931,290 A | 6/1990 | Rebhan | |
| 6,787,134 B1 | 9/2004 | Hokase | |

OTHER PUBLICATIONS

Smulski, Malinowski E., et al., "The effect of some drugs injection to pregnant heifers on blood antioxidant status.", Pol J Vet Sci., 2004, 7(2), 91-5.
Zadnik, T., et al., "Impact of Two Different Preventive Treatments on Milk Fever Incidence in Dry Dairy Cows", Krmiva 48 (2006), Zagreb, 6; 349-355.
Hollis, B. W., et al., "Vitamin D and Its Metabolites in Human and Bovine Milk", J. Nutr., 111: 1981, pp. 1240-1248.
Harris, Jr., Barney, "Vitamin Needs of Dairy Cattle", University of Florida, Cooperative Extension Service, Institute of Food and Agricultural Sciences, DS 27, Jun. 1991, pp. 1-5.
Sedgman, D.K., "How Does Parenteral Phosphorus and Vitamin D3 Correct Afebrile Postparturient Udder Edema in Goats?", Letter to the Editor, Can Vet J. Sep. 1982; 23(9):275.

*Primary Examiner* — Jennifer M Kim
(74) *Attorney, Agent, or Firm* — John D. Fado; G. Byron Stover

(57) ABSTRACT

Hydroxylated derivatives of vitamin D3 (cholecalciferol) and vitamin D2 (ergocalciferol) are effective for preventing or treating mastitis in animals. The hydroxylated derivatives of vitamins D3 or D2 are administered to the mammary gland of a female animal in an amount effective to inhibit or significantly reduce the growth of bacteria in the animal's mammary gland.

16 Claims, 4 Drawing Sheets

USE OF VITAMIN D IN DAIRY MASTITIS TREATMENT

CROSS-REFERENCE TO RELATED APPLICATIONS

This application claims the benefit under 35 U.S.C. 1.19(e) of U.S. provisional 61/473,208 filed Apr. 8, 2011, the contents of which are incorporated by reference herein.

BACKGROUND OF THE INVENTION

1. Field of the Invention

The invention relates to a method and composition for the prevention and treatment of mastitis in animals.

2. Description of the Prior Art

Mastitis is an inflammation of the mammary gland which occurs in animals in response to an injury therein. The disease is estimated to cost the United States economy approximately $2 billion per year. In dairy animals, mastitis usually occurs when bacteria invade the teat canal and mammary glands. These bacteria multiply and produce toxins (pyrogens) that cause injury to the milk secreting tissue and ducts throughout the mammary gland. In addition bacteria cause degradation of milk quality. This bacterial infection initiates an inflammatory response by the animal, stimulating the production of mediators of inflammation. Polymorphonuclear neutrophil (PMN) leukocytes, monocytes and other immune cells move to the site of infection, and masses of immune cells may pass between milk producing cells into the lumen of the alveoli, increasing the somatic cell counts (SCC) and further damaging secretory cells and milk quality (Virginia Cooperative Extension. 2011. Understanding the Basics of Mastitis. 404-233). Clots may form by aggregation of leukocytes and blood clotting factors and may block the ducts and prevent complete milk removal, resulting in scar formation and permanent loss of function of that portion of the mammary gland [Zhan and Khan. 2006. Pakistan Vet. J. 26(4):204-208].

Mastitis also causes significant changes to the milk from infected animals. The level of casein, the major milk protein of high nutritional quality, declines, while the level of lower quality whey proteins increases. An increase in SCC is also observed, and serum albumin, immunoglobulins, transferrin and other serum proteins pass into the milk. Other changes include increased conductivity, increased sodium and chloride concentrations, and decreased potassium and calcium concentrations (Virginia Cooperative Extension. ibid; Zhan and Khan. ibid).

The most common mastitis pathogens are found either in the udder (contagious pathogens) or the animal's surroundings (environmental pathogens), such as bedding, manure, soil, etc. Contagious mastitis pathogens (*Staphylococcus aureus, Streptococcus agalactiae*) are spread from infected udders to "clean" udders during the milking process through contaminated teatcup liners, milkers' hands, paper or cloth towels used to wash or dry more than one cow, and possibly by flies. Although new infections by environmental pathogens (other streptococci such as *Streptococcus uberis* and *Streptococcus dysgalactiae* and coliforms such as *Escherichia coli* and *Klebsiella pneuomoniae*) can occur during milking, primary exposure appears to be between milkings. Coliform infections are usually associated with an unsanitary environment (manure and/or dirty, wet conditions), while *Klebsiella* are found in sawdust that contains bark or soil. Approximately 70-80% of coliform infections become clinical (abnormal milk, udder swelling, or systemic symptoms that include swollen quarters, watery milk, high fever, depressed appetite or elevated body temperature). Environmental pathogens are often responsible for most of the clinical cases. About 50% of environmental streptococci infections display clinical symptoms (Virginia Cooperative Extension. ibid).

Conventional techniques for prevention of mastitis generally emphasize limiting exposure of the teats to potential pathogens by proper sanitation and minimizing access to contaminated environments such as mud, manure and stagnant water, teat dipping after milking, and culling of chronically infected animals. Antibiotic therapy is also utilized for animals at drying off (i.e., between lactation cycles). The current state-of-the-art treatment for mastitis in infected animals is antibiotic therapy (Virginia Cooperative Extension. ibid; Zhan and Khan. ibid). However, the use of antibiotics for treatment of milk-producing animals is a concern for many consumers and food safety advocates.

SUMMARY OF THE INVENTION

We have unexpectedly discovered that hydroxylated derivatives of vitamin D3 (cholecalciferol) and vitamin D2 (ergocalciferol) are effective for preventing or treating mastitis in animals. The hydroxylated derivatives of vitamins D3 or D2 are administered to the mammary gland of a female animal in an amount effective to inhibit or significantly reduce the growth of bacteria in the animal's mammary gland.

In accordance with this discovery, it is an object of this invention to provide an improved method and compositions for reducing the incidence and/or severity of mastitis in animals.

It is another object of this invention to provide a method and compositions for preventing and/or controlling mastitis in animals by inhibiting the growth of bacteria in the mammary gland of the animals.

A further object of this invention is to provide a method and compositions for preventing and/or controlling mastitis in animals with reduced or no use of antibiotics.

Yet another object of this invention is to reduce lost milk production from domestic animals such as dairy cattle by reducing the incidence, duration and/or severity of mastitis without the use of antibiotics.

Other objects and advantages of this invention will become readily apparent from the ensuing description.

DETAILED DESCRIPTION OF THE INVENTION

Figure 1:
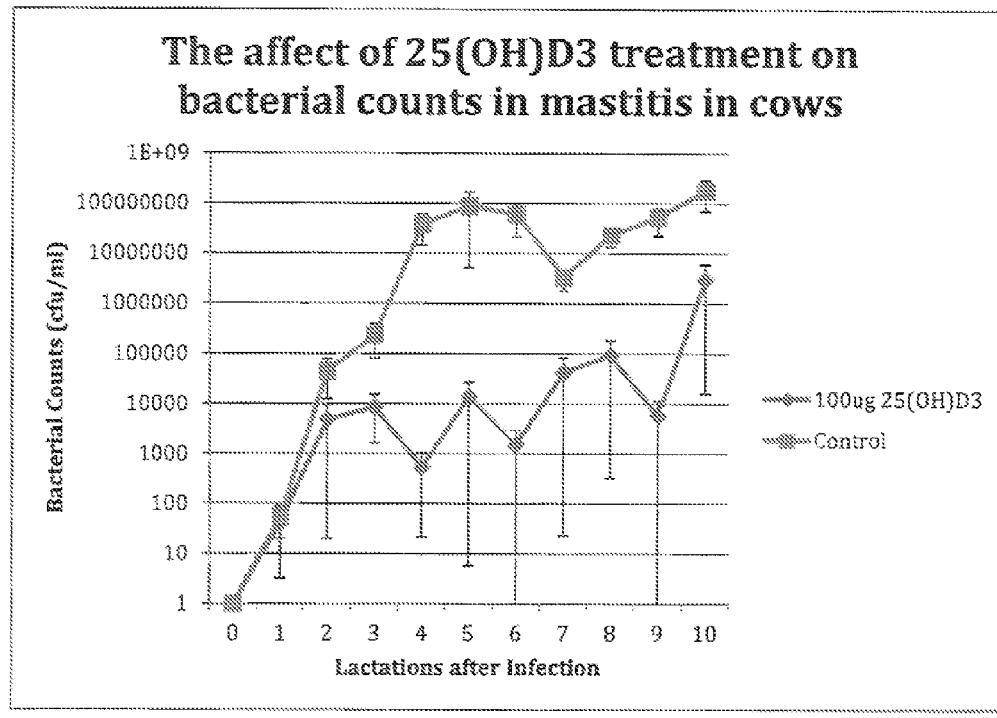
FIG. 1 shows the number of bacteria isolated from the 25-hydroxy vitamin D3 treated and control animals in Example 1.

According to the invention, the hydroxylated derivatives of vitamin D3 and hydroxylated derivatives of vitamin D2 are effective for controlling mastitis in animals when administered to the mammary gland thereof, significantly reducing the population levels of the bacterial pathogens causing the infection, and consequently eliminating or significantly reducing the clinical signs of mastitis, including reducing the inflammatory response by the animal. The preferred hydroxylated derivative of vitamins D3 or D2 for use herein is 25-hydroxy vitamin D3 (also referred to as 25-OH-D3 or 25-hydroxy-cholecalciferol or calcidiol). However, as the 25-hydroxy vitamin D3 is normally converted to the active form of vitamin D, 1,25-dihydroxy vitamin D3, it is envisioned that 1,25-dihydroxy vitamin D3 [also known as 1,25-(OH)$_2$-D3 or 1,25-dihydroxy-cholecalciferol or calcitriol] may be used. Other suitable compounds for use herein include 25-hydroxy-vitamin D2 (25-hydroxy-ergocalciferol) and 1,25-dihydroxy-vitamin D2 (25-hydroxy-ergocalciferol). It is also understood that a combination of one or more of the hydroxylated derivatives of vitamins D3 or D2 may be used herein. If used in combination the compounds may be administered separately or in admixture. Each of 25-hydroxy-vitamin D3; 1,25-dihydroxy-vitamin D3; 25-hydroxy-vitamin D2; and 1,25-dihydroxy-vitamin D2 may be obtained from commercial sources.

The method of this invention may be practiced with any animal susceptible to mastitis caused by a microbial infection. The invention may therefore be practiced with a wide variety of animals but is primarily used for the treatment of females and particularly domestic milk producing animals such as dairy cows. Alternatively, the method may be used for the treatment of female parent animals nursing young, such as swine, which may also be susceptible to mastitis. Without being limited thereto, animals which may be treated herein include bovine, swine, caprine or ovine. The method may be used for the treatment of animals which are lactating (including those in milk production as well as animals nursing young), milk producing animals between lactation cycles (dry periods), animals exhibiting active clinical mastitis infections, animals having subclinical mastitis infections, and healthy animals (e.g., administered prophylactically to prevent or limit the incidence or subsequent severity of infection).

Treatment of a subject animal with the hydroxylated derivative of vitamins D3 or D2 is preferably initiated as soon as possible after the diagnosis of mastitis infection. Depending upon the subject animal, this diagnosis is generally determined after the recognition of one or more symptoms associated with this infection. Such symptoms may include, for example: abnormal milk (particularly elevated SCC levels), udder swelling, or systemic symptoms that include swollen quarters, watery milk, high fever, depressed appetite, elevated body temperature, or detection of microorganisms (typically bacteria) within the animal's teat canal or mammary gland. Bacteria have been previously identified as causative agents of mastitis and thus the detection of which in the mammary gland is indicative of mastitis. The causative agents of mastitis include bacteria and other types of pathogens and include, but are not limited to: staphylococci including *Staphylococcus aureus, S. hyicus, S. epidermidis* and *S. capotus*, streptococci including *Streptococcus agalactiae, S. dysagalctiae, S. uberis* and *S. pyogenes, Corynebacterium* sp. such as *C. bovis, Brucella melitensis, Arcanobacterium pyogenes Mycoplasma* sp., *Mycobacterium tuberculosis, Escherichia coli, Pseudomonas* sp., *Klebsiella* sp., *Enterobacter aerogenes,* and *Proteus* sp. Although uncommon, algae have also been implicated as causative agents of mastitis, including *Prototheca zopfii* and *P. wickerhamii*. In any event, the diagnosis of infection with one of the above microbial pathogens is preferably subsequently confirmed by laboratory evaluation of mammary gland specimens.

In an alternative preferred embodiment, the hydroxylated derivative of vitamins D3 or D2 may be administered prophylactically to an animal to prevent or alleviate the manifestation of symptoms of a subsequent infection. In a particularly preferred embodiment, prophylactic treatment of an animal may be initiated with milk producing animals, most preferably dairy cows, which are between their lactation cycles (dry periods).

In use, the hydroxylated derivatives of vitamins D3 or D2 are administered to the mammary gland of a subject animal. Typically, the hydroxylated derivatives will be introduced into the udder or teat of the mammary gland, preferably by infusion of the mammary gland or using a teat cannula. In dairy cattle, the dosages are preferably administered subsequent to milking and continued until the mastitis has subsided, typically about 10 days.

The hydroxylated derivatives of vitamins D3 or D2 are administered in an amount effective to inhibit or control the growth of bacteria in the mammary gland of the animal. An effective amount is defined herein as that amount which will significantly reduce or eliminate the population(s) of bacteria within the mammary gland of a treated animal in comparison to an untreated control animal. A reduction of bacterial growth may be demonstrated by a significant reduction in the population of bacteria observed in the mammary gland or by a significant reduction in the severity or pathogenicity of infection, in comparison with untreated control animal. Without being limited thereto, the hydroxylated derivatives of vitamins D3 or D2 are administered in an amount effective to achieve at least a 1 log reduction in the bacterial populations in the mammary gland. Suitable amounts may be readily determined by the practitioner skilled in the art, and will vary with the specific subject animal, its size and physiological condition, and the particular hydroxylated derivative of vitamins D3 or D2 used, and may be determined by routine testing. For example, in bovine, the amount of 25-hydroxy-vitamin D3 in serum needs to be greater than 20 ng/ml to avoid major physiological disorders like hypocalcemia and rickets, and serum levels above 30-35 ng/ml are necessary for full immune cell's functionality. However, the levels of 25-hydroxy-vitamin D3 in normal milk are only 0.3-0.6 ng/ml. Thus innate immune cells are devoid of a source of 25-hydroxy-vitamin D3 once they enter the milk compartment. Consequently, the level of the hydroxylated derivatives of 25-hydroxy-vitamin D3 is selected to provide an increased level within the mammary gland. Without being limited thereto, suitable treatment doses of the hydroxylated derivative of vitamins D3 or D2 are typically greater than about 0.05 ng/kg and less than or equal to about 2 µg/kg of body weight of the treated animal, preferably greater than about 0.1 ng/kg and less than or equal to about 1.5 µg/kg of body weight, and most preferably greater than about 0.15 µg/kg and less than or equal to about 0.10 µg/kg of body weight. While higher amounts may be used, such amounts do not necessarily provide an increase in efficacy. The use of lower doses is particularly preferred for prolonged or prophylactic treatments. The number of treatment doses per day may vary with the number of milkings per day, and may be between one to three times per day and is preferably two or three times per day.

Although pure or substantially pure hydroxylated derivatives of vitamins D3 or D2 compounds may be administered to the animals directly, in an optional yet preferred embodiment they are further formulated with a conventional inert carrier or pharmaceutically acceptable carrier to facilitate administration. In a preferred embodiment, the hydroxylated derivatives of vitamins D3 or D2 are formulated with a proteinaceous carrier, most preferably vitamin D binding proteins such as found in fetal bovine serum (FBS). It is also envisioned that non-protein carriers such as physiologically buffered saline may be used. Adjuvants conventional in the art for the treatment of the animals, including those for the treatment of mastitis, may also be formulated with the compounds. In a particularly preferred embodiment, the hydroxylated derivative of vitamins D3 or D2 are administered with antibiotics, although the amount of the antibiotic is significantly lower than the dosage normally used for treatment of mastitis.

The following examples are intended only to further illustrate the invention and are not intended to limit the scope of the invention which is defined by the claims.

Example 1

In a first experiment, we infused 100 µg of 25(OH)D3 into an infected mammary quarter of two cows and showed increased gene expression of Cyp24A1 compared to cells obtained prior to 25(OH)D3 infusion. This observation demonstrated that gene expression of immune cells in the milk could be affected by a single infusion of vitamin D and that the cells in an infected gland are producing sufficient 1α-OHase to convert the 25(OH)D3 to 1,25(OH)$_2$D3 and subsequently cause the gene expression of Cyp24A1.

Figure 2:
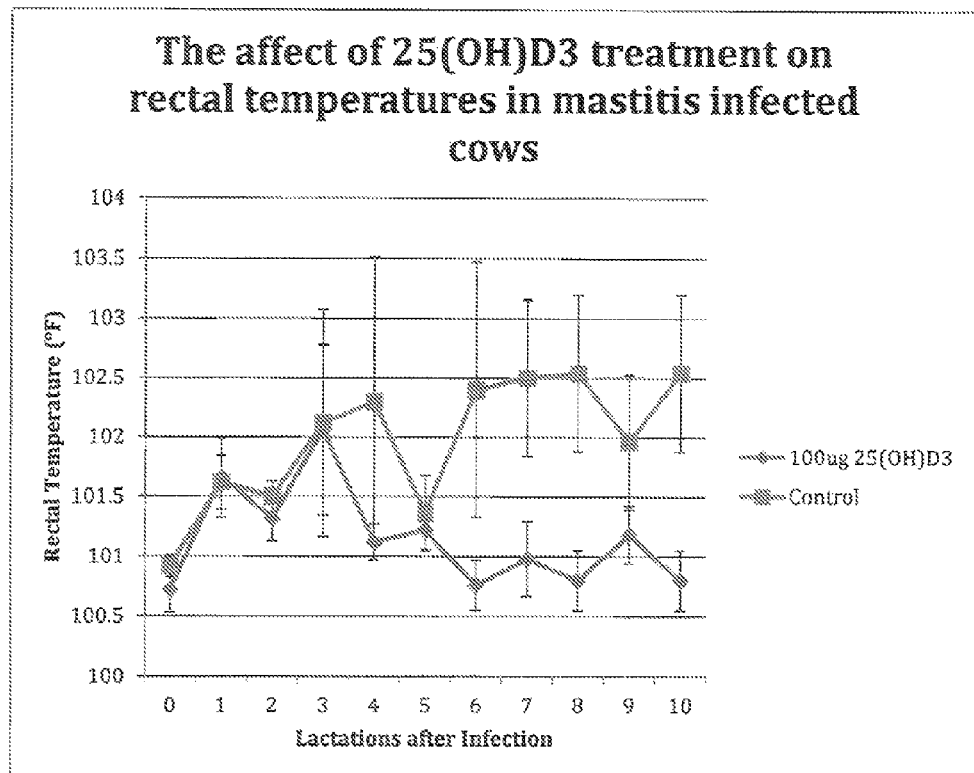
FIG. 2 shows significantly lower rectal temperatures in 25-hydroxy vitamin D3 treated cows at two time points ($p<0.05$) in Example 1.
Figure 3:
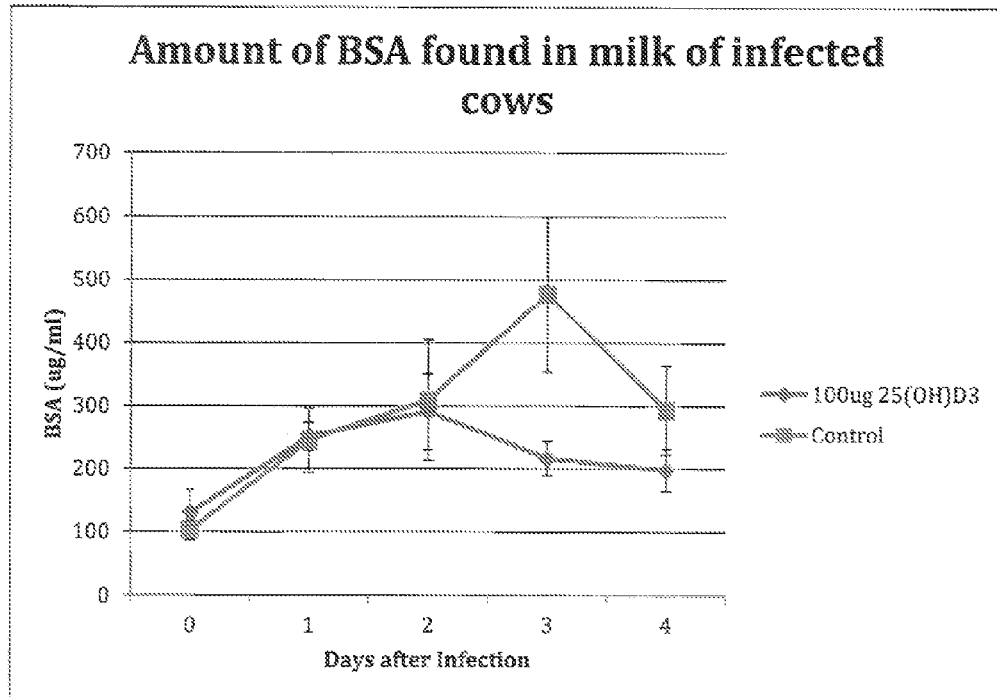
FIG. 3 shows the level of bovine serum albumin (BSA) in the milk from the 25-hydroxy vitamin D3 treated and control animals in Example 1.

To demonstrate the efficacy of the use of 25(OH)D3 as an intramammary immuno-modulator, we infected 14 animals with *S. uberis* by infusion of 500 cfu into one quarter of each mammary gland. Seven of the animals were treated after each milking with 100 µg of 25(OH)D3 in 10-ml fetal bovine serum (FBS), the other seven were sham treated with 10-ml FBS only. FIG. 1 shows the number of bacteria isolated from the vitamin D treated and control animals. The 100 µg 25(OH)D3 infusion resulted in a 2-4 log reduction in bacterial load on day 2 of the experiment and a 1.5-2 log reduction on days 4 and 5 post infection. Using repeated measures analysis, 25(OH)D3 significantly (p<0.05) reduced the bacterial counts in infected glands in the experiment with a significant difference (p<0.05) at two time points (day 2 AM and day 2 PM) (FIG. 1). This experiment did not affect the duration of the disease since both the vitamin D treated and control were infected throughout the entire experiment. FIG. 2 shows significantly lower rectal temperatures in 25(OH)D3 treated cows at two time points (p<0.05). The lower bacterial load in the 25(OH)D3 treated animals and therefore a likely reduction of pyrogens explains the reduction in fever seen in the treated group. The level of bovine serum albumin (BSA) in the milk is used as an indicator of changes in the mammary vascular permeability in the gland and typically increases with an acute infection. Although the data in FIG. 3 is not statistically significant, it does correlate with FIGS. 1 and 2. Fewer bacteria in the treated group (FIG. 1) leads to less tissue damage (FIG. 3) and leads to less pyrogens going systemic (FIG. 2). Also, after the fourth day of the infection two cows (out of 6) in the 25D3 had no infection, whereas, all six were infected at this time point in the control treated group.

Example 2

Figure 4:
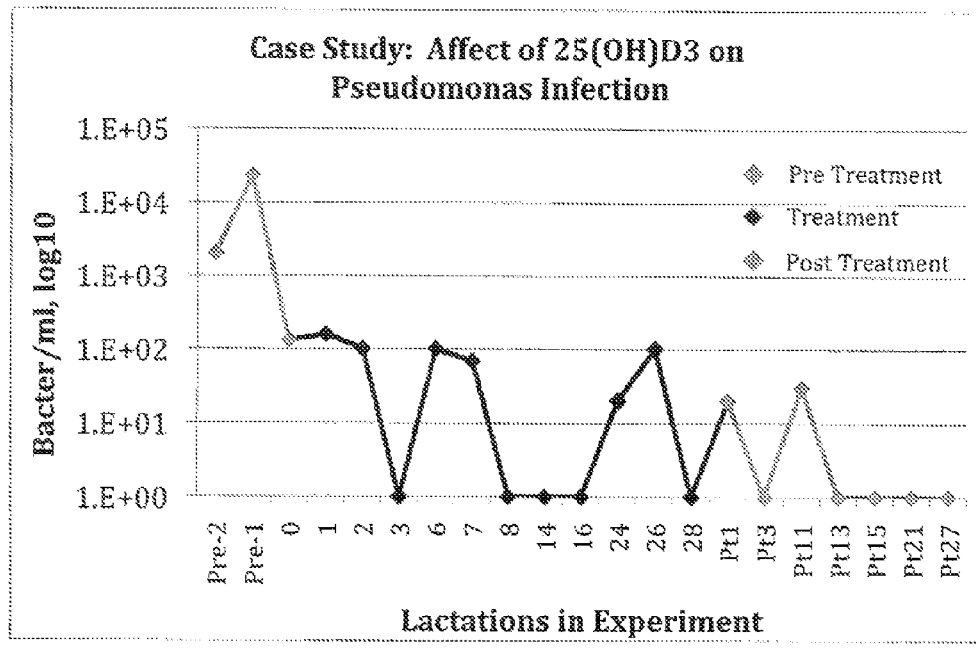
FIG. 4 shows the bacterial population loads in a mastitis-infected cow treated with 25-hydroxy vitamin D3 in Example 2.

A mastitis-infected cow that did not respond to typical mastitis treatments was shown to have a chronic *Pseudomonas* infection. After weeks of various conventional treatment the cow was treated with 25(OH)D3 as described in Example 1, with 100 ug infusions twice a day in the infected gland. The treatment of this animal with 25(OH)D3 caused the bacterial load to go from thousands of bacteria per ml to at or below our detection limit of 100 cfu/ml after 2 treatments (FIG. 4).

It is understood that the foregoing detailed description is given merely by way of illustration and that modifications and variations may be made therein without departing from the spirit and scope of the invention.

We claim:

1. A method for the treatment of mastitis in animals, comprising administering a composition comprising a hydroxylated derivative of vitamin D3 or vitamin D2 or combinations thereof to the mammary gland of a female animal in need thereof, in an amount effective to inhibit the growth of bacteria in the mammary gland of said animal wherein the hydroxylated derivative is selected from the group consisting of 25-hydroxy-vitamin D3 or 1,25-dihydroxy-cholecalciferol or 25-hydroxy-vitamin D2 or 1,25-dihydroxy-vitamin D2.

2. The method of claim 1 wherein said animal comprises a female bovine, swine, caprine or ovine.

3. The method of claim 2 wherein said animal comprises a dairy cow.

4. The method of claim 2 wherein said animal is lactating.

5. The method of claim 2 wherein said animal is between lactation cycles.

6. The method of claim 1 wherein said animal exhibits symptoms of an active mastitis infection.

7. The method of claim 1 wherein said animal does not exhibit symptoms of an active mastitis infection.

8. The method of claim 1 wherein said hydroxylated derivative is administered into the udder or teat of said mammary gland.

9. The method of claim 1 wherein said hydroxylated derivative is administered by infusion of the mammary gland or using a teat cannula.

10. The method of claim 1 wherein said hydroxylated derivative is formulated with a physiologically acceptable carrier.

11. The method of claim 10 wherein said carrier comprises a protein.

12. The method of claim 11 wherein said protein comprises a vitamin D binding protein.

13. The method of claim 10 wherein said hydroxylated derivative is further formulated with an antibiotic.

14. The method of claim 1 wherein said amount of said hydroxylated derivative is greater than about 0.05 ng/kg of body weight of said animal.

15. The method of claim 1 wherein said amount of said hydroxylated derivative is between about 0.05 ng/kg to 2 µg/kg of body weight of said animal.

16. The method of claim 15 wherein said amount of said hydroxylated derivative is between about 0.1 ng/kg to 1.5 µg/kg of body weight of said animal.

* * * * *